United States Patent [19]

Stiles et al.

[11] 4,137,271

[45] Jan. 30, 1979

[54] PROCESS FOR OXIDATION OF 1-PROPANOL

[75] Inventors: Alvin B. Stiles; David C. England, both of Wilmington, Del.

[73] Assignee: E. I. Du Pont de Nemours and Company, Wilmington, Del.

[21] Appl. No.: 837,631

[22] Filed: Sep. 28, 1977

Related U.S. Application Data

[62] Division of Ser. No. 639,246, Dec. 9, 1975, abandoned.

[51] Int. Cl.$^2$ .................. C07C 45/00; C07C 45/02
[52] U.S. Cl. ................................................. 260/604 R
[58] Field of Search .................. 260/465.3, 604 R, 682

[56] References Cited

U.S. PATENT DOCUMENTS

| | | | |
|---|---|---|---|
| 2,377,026 | 5/1945 | Miller | 260/682 |
| 2,540,587 | 2/1971 | Litton et al. | 260/682 X |
| 3,186,955 | 6/1965 | Callahan et al. | 260/465.3 X |
| 3,198,750 | 8/1965 | Callahan et al. | 260/465.3 X |
| 3,244,766 | 4/1966 | Keough | 260/682 |
| 3,328,315 | 6/1967 | Callahan et al. | 260/465.3 X |
| 3,365,482 | 1/1968 | Khoobiar | 260/465.3 |
| 3,427,343 | 2/1969 | Callahan et al. | 260/465.3 |
| 3,642,930 | 2/1972 | Grasselli et al. | 260/682 X |

FOREIGN PATENT DOCUMENTS

| | | | |
|---|---|---|---|
| 39-30263 | 12/1964 | Japan | 260/682 |
| 1233020 | 5/1971 | United Kingdom | 260/682 |

*Primary Examiner*—Joseph Paul Brust

[57] ABSTRACT

Acrylic products are produced in high yields by a catalytic process in which a vaporous mixture of 1-propanol and oxygen are contacted in rapid sequence with (1) a dehydration catalyst and (2) an oxidation catalyst.

4 Claims, No Drawings

PROCESS FOR OXIDATION OF 1-PROPANOL

CROSS REFERENCE TO RELATED APPLICATIONS

This application is a divisional application of our copending application Ser. No. 639,246, filed Dec. 9, 1975, now abandoned.

The invention is directed to a process for the oxidation of 1-propanol. In particular, it is directed to a process for the oxidation and ammoxidation of 1-propanol to form acrolein and acrylonitrile, respectively.

BACKGROUND OF THE INVENTION

Commercial preparations of acrolein and acrylonitrile have heretofore involved the oxidation and the ammoxidation of propylene, respectively.

However, because of the widely fluctuating availibility of various chemical feedstocks, it would be desirable to prepare acrolein and acrylonitrile from a propanol. One way to accomplish this would be to dehydrate the propanol catalytically and then oxidize or ammoxidize the resulting propylene by the known catalytic processes. Such a two-step process would obviously be more expensive than preparation directly from propylene.

Another possible solution would be to use the known catalysts in a single-step process of direct oxidation or ammoxidation of a propanol. This has been found to produce the desired acrolein and acrylonitrile, respectively, but in substantially lower yields than are obtained from propylene.

BRIEF DESCRIPTION OF THE INVENTION

It has now been discovered that when 1-propanol and oxygen (without or with ammonia) are passed under conditions for vapor phase oxidation (or ammoxidation) through a two-stage catalyst system consisting of a first bed of a dehydration catalyst and an adjacent second bed of an oxidation catalyst, the yield of acrylic compounds is substantially greater than when the first bed of dehydration catalyst is absent or when the contents of the two catalyst beds are mixed together to form a single bed.

In particular, the invention is directed to a process for the oxidation of 1-propanol to form acrylic compounds comprising the steps (a) forming a vaporous admixture comprising 0.5–5 moles of $O_2$ per mole of 1-propanol; and (b) contacting the vaporous admixture in rapid sequence with a two-stage catalyst system for a period of at least 0.1 second in each stage at a temperature of 250°–640° C. and pressure of 0.5–6 atmospheres, the catalyst system comprising (1) a first bed of dehydration catalyst and
(2) a second bed of oxidation catalyst.

In one preferred aspect of the invention, the process is carried out with ammonia in the feed gas as well. This process results in ammoxidation of the 1-propanol to obtain high yields of acrylonitrile in place of acrolein. As used herein, the term "ammoxidation" has its accepted meaning of oxidation in the presence of ammonia.

DESCRIPTION OF THE PRIOR ART

It is, of course, well known to oxidize propylene directly to acrolein and, to a lesser extent, it is also known to oxidize 1-propanol to obtain acrolein or, when ammonia is present, acrylonitrile.

For example, U.S. Pat. No. 2,904,580 to Idol discloses the ammoxidation of propylene using as oxidation catalyst the bismuth, tin and antimony salts of molybdic and phosphomolybdic acids. In U.S. Pat. No. 3,186,955, Callahan et al. disclose the use of bismuth molybdates or phosphomolybdate with barium and silicon oxides for the oxidation and ammoxidation of olefins. Similarly, Callahan et al. in U.S. Pat. No. 3,198,750 and U.S. Pat. No. 3,308,151 disclose the use of mixed antimony and uranium oxides as catalysts for both the oxidation and dehydrogenation of olefins. A rather different catalyst for the oxidation of olefins is revealed by Young in U.S. Pat. No. 3,547,984. This catalyst is carbollide (carbon and boron containing ligand) complex with a Group VIII metal. In U.S. Pat. No. 3,799,978, the oxidation of $C_3$ and higher olefins is disclosed using a catalyst containing cobalt, iron, bismuth, tungsten, molybdenum, silicon and alkaline earth metal. Furthermore, a catalyst related to the one described in the Callahan U.S. Pat. No. 3,198,750 referred to above is disclosed in U.S. Pat. No. 3,886,096 to Li. This catalyst contains iron and tungsten in addition to antimony and uranium. Finally, U.K. Pat. No. 1,319,190 to The Standard Oil Company shows the oxidation or ammoxidation of either propylene or butylene with a catalyst containing a mixture of several metal oxides with bismuth, molybdenum and iron.

Though there is considerable prior art relating to the oxidation/ammoxidation of olefins, comparatively little has been disclosed on the ammoxidation of non-olefinic materials. Among these, however, is U.S. Pat. No. 3,365,482 to Khoobiar who discloses the vapor phase ammoxidation of e.g., 1-propanol, propionic acid or propionaldehyde to form acrylonitrile using a tungsten or molybdenum catalyst supported on activated alumina. The vapor phase oxidation of isopropanol (2-propanol) using a molybdenum and tellurium oxide catalyst is disclosed in U.K. Pat. No. 1,069,446 to Imperial Chemical Industries.

The liquid phase dehydration of aliphatic diols is disclosed using a "bleaching earth" as catalyst in U.S. Pat. No. 1,672,378 to Freund. In German Patent 600,002, Plauson discloses the vapor phase dehydration of alcohols or cracking of hydrocarbons using a molten catalyst containing phosphoric acid or boric acid in admixture with fluosilicic acid metal salts.

Thus, while the ammoxidation of 1-propanol to acrylonitrile with a single catalyst was known and the dehydration of 1-propanol to form olefins was also known, the prior art is completely silent as to the combination of these functions in any advantageous way.

DETAILED DESCRIPTION OF THE INVENTION

The process of the invention is characterized by at least two surprisingly critical aspects: (1) the process appears to be unique to 1-propanol; and (2) only certain carefully selected combinations of particular oxidation and dehydration catalysts can be used effectively.

Thus, of the many catalysts capable of oxidizing or ammoxidizing 1-propanol to acrolein or acrylonitrile, only selected ones are benefitted by pretreatment of the feed over a dehydration catalyst. Conversely, only selected dehydration catalysts have been found to be effective to upgrade the activity of the subsequent oxidation catalyst.

Dehydration catalysts which enhance the activity of catalysts for oxidation and ammoxidation of 1-propanol in the two-bed catalyst system of this invention are illustrated by boron phosphate, coprecipitated $SiO_2/Al_2O_3$ and coprecipitated $WO_3/Al_2O_3$.

Catalysts for oxidation and ammoxidation of 1-propanol whose activity is enhanced in the two-bed catalyst system of this invention include the following:

(1) mixed oxides of Fe, Co, Ni, Bi, P, Mo and K;
(2) mixed oxides of Fe, Co, W, Bi, Mo and Mg;
(3) mixed oxides of Sb and U; and
(4) bismuth molybdate and bismuth phosphomolybdate.

The catalysts may be unsupported or supported on known catalyst supports such as silica, silica-alumina, alumina and the like. The preparation of such catalysts, whether supported or not, can be done by a number of techniques well known in the art. Illustrations of the techniques useful for preparation of the oxidation catalysts are given in the references which are summarized hereinabove.

The reactants in the process of this invention include 1-propanol, oxygen and optionally ammonia. Other materials which are inert to oxidation and ammoxidation under the conditions employed may also be present, even in major amounts. Thus, inert gases such as nitrogen, helium and the like may be employed as carrier gases. Pure oxygen may be employed but air is the preferred source of oxygen. Carbon dioxide, carbon monoxide and water vapor may be introduced and they are always present in the product stream. Minor amounts of methanol may be present, but this is usually to be avoided since it consumes reactant oxygen and produces byproduct oxidation products which are less valuable and which complicate separation procedures. Isobutanol may also be present. In the oxidation mode of the invention, isobutanol yields primarily methacrolein and in the ammoxidation mode it yields primarily methacrylonitrile. These may be readily separated from the acrolein and/or acrylonitrile produced, for example, by distillation.

The molar ratio of oxygen to alcohol in the feed to the reactor should be in the range from 0.5:1 to 5:1 and ratios from 1:1 to 3:1 appear to be optimum and are therefore preferred.

When it is desired to produce acrylonitrile in the process of this invention, ammonia is added to the feed gas along with the 1-propanol and oxygen. The molar ratio of ammonia to alcohol in the feed may vary in the range from 0:1 to 5:1. Excess ammonia above that in the latter ratio may be present but it produces no further beneficial effect. Ratios of 1:1 to 3:1 are preferred for nitrile production, since they give higher yields and fewer byproducts.

The process of the invention can be carried out at any temperature above the threshold temperature of the catalysts and up to about 600° C. Above about 600° C., the reactions tend to proceed out of control to complete carbonization. On the other hand, the threshold temperature of most catalysts is above about 250° C. Thus, a temperature range of 350° to 500° C. will ordinarily be preferred since within this range both adequate reaction rate and a low degree of carbonization are obtained.

The apparent contact time of the feed gas with each of the two catalyst beds in the process of this invention should be in the range of 0.1 to 60 seconds, contact times of 0.3 to 20 seconds being preferred. Contact times may be varied by changing the flow rate of the feed gas and by changing the depth of the catalyst beds. Ordinarily, the least possible contact time consistent with effective contact with the catalytic surface is to be preferred in order to minimize side reactions occurring on the catalyst surface, deposits from which tend to reduce catalyst activity and life.

The pressure at which the reaction is carried out may vary widely from 0.5 to 10 atmospheres or even higher so long as vapor phase conditions are maintained. However, to keep temperatures down and to maintain optimum reactant concentrations, it is preferred to operate within the range of 1 to 3 atmospheres.

The catalyst particles may vary in size from lumps or pellets with a maximum dimension of up to 15 mm through granules to powders fine enough to pass a 100 mesh screen. The particles may be deployed in any form suited to bring them in contact with the feed gas. There is no apparent theoretical reason why either or both catalytic stages could not be practiced in either fixed, moving or fluidized beds. However, engineering economics will usually result in a preference for fixed bed operation of both stages. In fixed bed operations, catalyst particle size will be largely governed by pressure drop considerations.

In order to reduce the incidence of the reactions proceeding to carbonization, it is not only desirable to minimize catalyst contact times as discussed hereinabove but also desirable to minimize the time elapsed between the two catalytic stages. Consequently, it is preferred that the product for the dehydration catalysis stage be passed almost immediately to the oxidation catalysis stage without cooling. Ordinarily, this will be accomplished by placing one of the catalyst beds on top of the other in a single vertical reactor in which the flow is such that the gas stream passes first through the dehydration catalyst and then through the oxidation catalyst.

Further in this regard, a still further advantage of the process of the invention is that it generates water. Therefore, unlike other exothermic catalytic processes, such as the catalytic oxidation of propylene, it is unnecessary to add water to the reaction for the purpose of reducing the deposition of carbon on the catalyst.

The process of the invention may be carried out intermittently or on a continuous basis, the latter being preferred for commercial operation. The products formed are separated and recovered by known means, such as fractional distillation and absorption. Recycling of unreacted propanol and/or ammonia is anticipated.

An important advantage of the process of the invention is the fact that the dehydration stage is endothermic and the oxidation stage is exothermic. Thus, the process is nearly heat balanced overall, which makes it easy to control. It is preferred to take advantage of the mixed thermicity of the process by using in the process a multiple bed reactor in which fresh feed is heated to reaction temperature and passed through a first bed of dehydration catalyst. The dehydration product therefrom, cooled as a result of the endothermic nature of the reaction, is passed to a second bed containing oxidation catalyst. The oxidized product from the second bed, which would be hot as a result of the exothermic character of the reaction, is mixed with fresh cold feed gas in an amount such that the desired temperature for the subsequent dehydration reaction is reached, and the mixture is passed to a third bed containing dehydration catalyst. The resultant cool dehydration reaction product is then passed to a further bed of oxidation catalyst, and so on for as many stages as may be desired. Even higher heat recovery is possible in alternating bed reactors of this sort when the hot product from the last oxidation stage is used to exchange heat with fresh feed to the initial dehydration stage.

In the examples which follow the following experimental procedures were employed:

Ammoxidation Procedure

A vertical reactor was made by providing a 150 mm length of 16 mm I.D. stainless steel tubing with fittings at both ends for conducting gases in and out and with a 3 mm O.D. stainless steel thermocouple well running lengthwise through the center of the tube and supported from the upper fitting. The bottom end of the thermocouple well carried a horizontal stainless steel perforated disc which fit snugly against the sides of the reactor and supported the catalysts. Particulate catalysts screened to 8-20 mesh size were poured into the top of the reactor. Gas flow through the reactor was from top to bottom so that the first catalyst bed encountered by the feed gas was the last one poured in. In all the accompanying designations wherever two catalyst beds are used, the "first" catalyst bed is the first one encountered by the feed gas. The catalysts operated as fixed beds. The feed gas consisted of 7 cc/min vaporized 1-propanol, 11 cc/min pure oxygen, 7 cc/min ammonia and 44 cc/min helium, all rates measured at atmospheric pressure. The reactor and gas inlet tubes were externally heated and temperatures were measured by the thermocouple in the middle of the catalyst bed. This procedure provided a contact time of about 1.5 sec for a 5 cc catalyst bed and about 3.0 sec for a 10 cc catalyst bed. Product gases obtained from the bottom of the reactor were analyzed by gas chromatography. Yield values shown are based on 1-propanol. Ammoxidations carried out by this procedure are summarized in Table 1, including the comparison experiments which confirm the value of the invention.

Oxidation Procedure

A vertical reactor was made by providing a 21 cm length of 26 mm O.D. quartz tubing with ball joint fittings at either end for conducting gases in and out and with a 5 mm O.D. quartz thermocouple well running lengthwise through the center of the tube and supported from the bottom of the reactor. Near the bottom of the tube a plug of quartz wool fitted snugly against the sides of the reactor and the thermocouple well to support the catalysts. Particulate catalysts screened to 10-20 mesh size (except where indicated) were poured into the top of the reactor. Gas flow through the reactor was from top to bottom so that the first catalyst bed encountered by the feed gas was the last one poured in. In all the accompanying designations wherever two catalyst beds are used, the "first" catalyst bed is the first one encountered by the feed gas. The catalysts operated as fixed beds. The reactor and gas inlet tubes were externally heated and temperatures were measured by the thermocouple in the middle of the catalyst bed. Feed gas flow rates were adjusted to provide a contact time of about 1 sec for a 5 cc catalyst bed and about 2 sec for a 10 cc catalyst bed. Product gases obtained from the bottom of the reactor were analyzed by gas chromatography. Yield values shown are based on 1-propanol. Oxidations carried out by this procedure are summarized in Table 2, including the comparison experiments which confirm the value of the invention.

In the examples proportions are by weight unless otherwise indicated.

EXAMPLE 1

In the ammoxidation procedures described above the first catalyst bed encountered by the feed gas was 10 cc of coprecipitated $SiO_2/Al_2O_3$ containing 13% $Al_2O_3$. The second catalyst bed was 5 cc of Catalyst "A" which consists of mixed oxides of Ni, Co, Fe, Bi, P, Mo and K supported on silica which comprises 50% of the catalyst by weight. The catalyst was pelleted, crushed and screened to 8-20 mesh before use. This Catalyst "A" is essentially identical to the catalyst shown in Examples 11 and 15 of British Pat. No. 1,319,190 referred to hereinabove. The results shown in Table 1 indicate that good yields of acrylonitrile are obtained.

EXAMPLE 2

The procedure of Example 1 was repeated with the exception that 10 cc of boron phosphate was used as the first catalyst bed in place of 10 cc of $SiO_2/Al_2O_3$ (Run No. 2). Comparison experiments were as follows.

Run No. 3. The procedure of Run No. 1 was repeated with the exception that the first bed of dehydration catalyst (10 cc of coprecipitated $SiO_2/Al_2O_3$) was omitted.

Run No. 4. The procedure of Run No. 1 was repeated with the exception that the two catalyst beds were replaced by a single bed consisting of a thorough mixture of 5 cc of $SiO_2/Al_2O_3$ (13% $Al_2O_3$) with 5 cc of Catalyst "A".

Run No. 5. The procedure of Run No. 4 was repeated with the exception that 5 cc of $SiO_2/Al_2O_3$ (13% $Al_2O_3$) was added as a first catalyst bed over the mixed catalyst bed which served as the second catalyst bed.

Run No. 6. The procedure of Run No. 1 was repeated with the exception that 10 cc of $AlPO_4$ was used as a first catalyst bed in place of 10 cc of $SiO_2/Al_2O_3$.

From a comparison of Runs No. 1 and 2, it can be seen that the borom phosphate is a more effective first stage catalyst than the silica/alumina when used in this sequence. Runs No. 3 and 4 illustrate quite graphically the importance of the dehydration function and the requirement that it be a discreet stage rather than simultaneous with the oxidation function. Furthermore, it is quite clearly shown that the aluminum phosphate is not suitable for use as a dehydration catalyst in the process of the invention.

EXAMPLE 3

In the ammoxidation procedure described above the first catalyst bed encountered by the feed gas was 10 cc of boron phosphate (Run No. 7). The second catalyst bed was 5 cc of Catalyst "B" which was pelleted, cut and screened to 8-20 mesh before use. It consists of mixed oxides of Sb and U supported on silica which comprises 50% of the catalyst. This catalyst is like the catalyst shown in Examples 12 and 13 of U.S. Pat. No. 3,198,750 (Aug. 3, 1965 to Standard Oil Company) with the exception that the Sb:U molar ratio is 4.6:1 instead of 4.9:1. The results which are shown in Table 1 indicate a substantially lower yield than was obtained with Catalyst "A". However, the process was quite selective in that proportions of acetonitrile were quite small and only trace amounts of propionitrile were present.

EXAMPLE 4

The procedure of Example 3 was repeated with the exception that 10 cc of coprecipitated $SiO_2/Al_2O_3$ (13% $Al_2O_3$) was used as the first catalyst bed in place of 10 cc of boron phosphate (Run No. 8).

Comparison experiments for Examples 3 and 4 were as follows:

Run No. 9. The procedure of Run No. 7 was repeated with the exception that the first bed of dehydration catalyst (10 cc of boron phosphate) was omitted.

Run No. 10. The procedure of Run No. 7 was repeated with the exception that the two catalyst beds were replaced by a single bed consisting of a thorough mixture of 5 cc of $SiO_2/Al_2O_3$ (13% $Al_2O_3$) with 5 cc of Catalyst "B".

Run No. 11. The procedure of Run No. 10 was repeated with the exception that 5 cc of $SiO_2/Al_2O_3$ (13% $Al_2O_3$) was added as a first catalyst bed over the mixed catalyst bed.

The data for Runs 8 through 11 confirm the findings of Example 2 as to the importance of the dehydration function and the requirement that it be a discreet stage.

EXAMPLE 5

In the ammoxidation procedure described above, the first catalyst bed encountered by the feed gas was 10 cc of boron phosphate. The second catalyst bed was 5 cc of bismuth phosphomolybdate supported on 50% by weight of $SiO_2$, prepared as shown in Example 1 of U.S. Pat. No. 2,904,580 referred to above (Run No. 12).

For comparison, Run No. 13 was carried out in the same manner with the exception that the first catalyst bed (10 cc of boron phosphate) was omitted. The result of this was reduction of the acrylonitrile yield by over 50% from 58.1% to only 28.2% (See Table 1 below).

Additional comparison experiments for Examples 1–5 were also conducted as follows:

Run No. 14. In the ammoxidation procedure described above only a single catalyst bed comprising 5 cc of bismuth niobate (approximately $BiNbO_4$) was employed.

The procedure of Run No. 14 was repeated with the exception that 10 cc of boron phosphate was added as a first catalyst bed over the bismuth niobate which served as the second catalyst bed (Run No. 15). The increase in acrylonitrile over Run No. 14 was not significantly beyond the limit of experimental error.

Run No. 16. In the ammoxidation procedure described above only a single catalyst bed comprising 5 cc of bismuth tantalate (approximately $BiTaO_4$) was employed.

Run No. 17. The procedure of Run No. 16 was repeated with the exception that 10 cc of boron phosphate was added as a first catalyst bed over the bismuth tantalate which served as the second catalyst bed (Run No. 17). The increase in acrylonitrile over Run No. 16 was about at the limit of experimental error.

When propylene was substituted for 1-propanol in the feed gas in the procedure of Run No. 3, the yield of acrylontrile was 59% (Run No. 18).

TABLE 1

| Example | Run No. | Dehydration Catalyst (first catalyst, if present) | Ammoxidation Catalyst | Temp. °C | % Yield Acrylo-nitrile | Aceto-nitrile | Propio-nitrile | $CO_2$ | CO | HCN |
|---|---|---|---|---|---|---|---|---|---|---|
| 1 | 1 | 10 cc $SiO_2/Al_2O_3$ | 5 cc "A" | 428 | 40.4 | 16.6 | 5.1 | 22.5 | 4.9 | 0.2 |
| 2 | 2 | 10 cc boron phosphate | 5 cc "A" | 428 | 56.2 | 24.3 | (trace) | 11.6 | 3.1 | (trace) |
|  | 3 |  | 5 cc "A" | 420 | 35.9 | 28.7 | 18.5 | 15.3 | 5.1 | 7.1 |
|  | 4 |  | 5 cc $SiO_2/Al_2O_3$ / 5 cc "A" mixture | 429 | 25.4 | 28.0 | 13.4 | 20.6 | 7.6 | 2.4 |
|  | 5 | 5 cc $SiO_3/Al_2O_3$ | 5 cc $SiO_2/Al_2O_3$ / 5 cc "A" mixture | 419 | 20.5 | 21.7 | 11.1 | 25.1 | 7.7 | 0.6 |
|  | 6 |  | 5 cc $AlPO_4$ / 5 cc "A" | 418 | 19.8 | 24.5 | 13.6 | 23.2 | 8.5 | (trace) |
| 3 | 7 | 10 cc boron phosphate | 5 cc "B" | 422 | 26.3 | 7.6 | (trace) | 26.8 | (trace) | 0.7 |
| 4 | 8 | 10 cc $SiO_2/Al_2O_3$ | 5 cc "B" | 424 | 15.2 | 17.0 | 11.6 | 23.0 | 5.7 | 1.3 |
|  | 9 |  | 5 cc "B" | 432 | 5.2 | 0.4 | (trace) | 31.8 | 9.6 | 3.1 |
|  | 10 |  | 5 cc $SiO_2/Al_2O_3$ / 5 cc "B" mixture | 416 | 2.5 | 13.6 | 12.1 | 30.7 | 10.5 | (trace) |
|  | 11 | 5 cc $SiO_2/Al_2O_3$ | 5 cc $SiO_2/Al_2O_3$ / 5 cc "B" mixture | 420 | 3.5 | 13.3 | 9.1 | 26.1 | 7.6 | (trace) |
| 5 | 12 | 10 cc boron phosphate | 5 cc bismuth phosphomolybdate | 441 | 58.1 | 9.5 | (trace) | 12.9 | 4.9 | 0.9 |
|  | 13 |  | 5 cc bismuth phosphomolybdate | 425 | 28.2 | 15.5 | (trace) | 18.8 | 4.7 | 2.6 |
|  | 14 |  | 5 cc bismuth niobate | 430 | 5.6 | 17.0 |  | 53.8 |  |  |
|  | 15 | 10 cc boron phosphate | 5 cc bismuth niobate | 423 | 7.6 | 3.5 |  | 6.3 |  |  |
|  | 16 |  | 5 cc bismuth tantalate | 453 | 6.7 | 6.0 |  | 51.8 |  | 3.3 |
|  | 17 | 10 cc boron phosphate | 5 cc bismuth tantalate | 419 | 7.6 | 2.7 |  | 11.8 |  | 0.6 |
|  | 18 |  | 5 cc "A" | 420 | 59 |  |  |  |  |  |

EXAMPLE 6

In the oxidation procedure described above a feed gas mixture of 6 volume percent 1-propanol, 15 volume percent oxygen and 79 volume percent helium was used. The first catalyst bed encountered by the feed gas was 5 cc of boron phosphate. The second catalyst bed was 5 cc of Catalyst "A" (about 100 mesh) (Run No. 19).

A comparison experiment for Run No. 19 was as follows:

Run No. 20. The procedure of Run No. 19 was repeated with the exception that the first catalyst bed (5 cc of boron phosphate) was omitted. The results, which are given in Table 2, show once again the same quite startling effect upon acrolein yield as was previously shown with respect to acrylonitrile yields.

EXAMPLE 7

In the oxidation procedure described above the 6/15/79 volume ratio feed gas of Example 6 was used. The first catalyst bed encountered by the feed gas was 5 cc of boron phosphate. The second catalyst bed was 10 cc of a pelleted catalyst of the mixed oxides of Co, Fe, Bi, W, Mo and Mg supported on $SiO_2$ and prepared as shown in Example 1 of U.S. Pat. No. 3,799,978 referred to above (Run No. 21). This catalyst is referred to as catalyst "C" in Table 2. The results shown in Table 2 are quite similar to those obtained in Run No. 19.

EXAMPLE 8

In the oxidation procedure described above, a feed gas mixture of 7 volume percent 1-propanol, 15 volume percent oxygen and 78 volume percent helium was used. The first catalyst bed encountered by the feed gas was 5 cc of 10% $WO_3$ on $Al_2O_3$ (Catalyst W-010, Harshaw Chemical Co.). The second catalyst bed was 5 cc of the mixed oxide catalyst "C" shown in Run No. 21 (Run No. 22). In a second run of this system (Run No. 23) a feed gas ratio of 2/16/82 volume percentages of the above ingredients was used.

Comparison experiments for Example 7 and 8 were as follows:

Run No. 24. The procedure of Run No. 21 was repeated with the exception that the first catalyst bed (5 cc of boron phosphate) was omitted.

Run No. 25. The procedure of Run No. 21 was repeated with the exception that the first catalyst bed was 5 cc of $Al_2O_3$ (Catalyst A-0104, Harshaw Chemical Co.) instead of 5 cc of boron phosphate.

The data in Table 2 again show the importance of the prior dehydration stage. Furthermore, it is particularly interesting to note from Run No. 25 that the effect of using $Al_2O_3$ as dehydration catalyst was worse than if no catalyst had been used at all.

EXAMPLE 9

In the oxidation procedure described above a feed gas mixture of 11 volume percent 1-propanol, 16 volume percent oxygen and 73 volume percent helium was used. The first catalyst bed encountered by the feed gas was 5 cc of boron phosphate. The second catalyst bed was 5 cc of a commercial bismuth phosphomolybdate catalyst supported on 50% by weight of $SiO_2$, Catalyst "D", about 100 mesh, as purchased. Separate runs were made at 425° C., 450° C. and 475° C. (Runs No. 26–28). Results are shown in Table 2.

Comparison experiments for Example 9 were as follows.

Runs No. 29–31. The procedures of Runs No. 26–28 were repeated with the exception that the first catalyst bed (5 cc of boron phosphate) was omitted.

Runs No. 32–34. When a 12/8/14/66 volume percentage mixture of water vapor/propylene/oxygen/helium was used as feed gas in procedures otherwise like those of Runs 29–31, yields of acrolein were 76% at 425° C., 77% at 450° C. and 71% at 475° C.

Comparison of Runs 29–31 with Runs 26–28 again show the essential nature of the first catalyst stage when 1-propanol is used as the basic feedstock. However, this is, of course, not required for the oxidation of propylene, as is shown by the acrolein yields in Runs 32–34.

In addition to the marked specificity of the catalytic species which can be used in the process of the invention, it is surprising too that when 2-propanol is substituted for 1-propanol, there is utterly no enhancement of either oxidative or ammoxidative activity.

TABLE 2

| Example | Run No. | Dehydration Catalyst (first catalyst, if present) | Oxidation Catalyst | Temp. °C | % Yield Acrolein | Acet-aldehyde | Propylene | $CO_2$ | CO | Acids |
|---|---|---|---|---|---|---|---|---|---|---|
| 6 | 19 | 5 cc boron phosphate | 5 cc "A" | 430 | 57 | (trace) | 33 | 6 | 1 | 4 |
|   | 20 |   | 5 cc 37 A" | 435 | 22 | 1 | 15 | 23 | 25 | 14 |
| 7 | 21 | 5 cc boron phosphate | 10 cc catalyst "C" | 375 | 54 | 1 | 35 | 4 | (trace) | 7 |
| 8 | 22 | 5 cc $WO_3/Al_2O_3$ | 10 cc catalyst "C" | 375 | 49 | 2 | 33 | 8 | 5 | 4 |
|   | 23 | 5 cc $WO_3/Al_2O_3$ | 10 cc catalyst "C" | 375 | 43 | (trace) | 15 | 14 | 25 | 4 |
|   | 24 |   | 10 cc catalyst "C" | 375 | 37 | 3 | 25 | 12 | 11 | 12 |
|   | 25 | 5 cc $Al_2O_3$ | 10 cc catalyst "C" | 375 | 16 | 2 | 22 | 34 | 22 | 3 |
| 9 | 26 | 5 cc boron phosphate | 5 cc "D" | 425 | 36 | 2 | 51 | 5 | 3 | 2 |
|   | 27 | 5 cc boron phosphate | 5 cc "D" | 450 | 49 | 3 | 34 | 8 | 4 | 2 |
|   | 28 | 5 cc boron phosphate | 5 cc "D" | 475 | 54 | 3 | 24 | 11 | 7 | 2 |
|   | 29 |   | 5 cc "D" | 425 | 15 | 7 | 54 | 10 | 9 | 4 |
|   | 30 |   | 5 cc "D" | 450 | 22 | 6 | 43 | 12 | 13 | 3 |
|   | 31 |   | 5 cc "D" | 475 | 12 | 6 | 40 | 20 | 18 | 3 |
|   | 32 |   | 5 cc "D" | 425 | 76 |   |   |   |   |   |
|   | 33 |   | 5 cc "D" | 450 | 77 |   |   |   |   |   |
|   | 34 |   | 5 cc "D" | 475 | 71 |   |   |   |   |   |

We claim:

1. A process for the oxidation of 1-propanol to acrolein comprising the steps
   (a) forming a vaporous admixture comprising 0.5–5 moles of $O_2$ per mole of 1-propanol; and
   (b) contacting the vaporous admixture in rapid sequence with a two-stage catalyst system for a period of from 0.1 to 60 seconds in each stage at a temperature of from 350 to 500° C. and at a pressure of 0.5–6 atm, the catalyst system consisting essentially of
      (1) a first bed of dehydration catalyst selected from the group consisting of boron phosphate, coprecipitated $SiO_2/Al_2O_3$ and coprecipitated $WO_3/Al_2O_3$; and
      (2) a second bed of oxidation catalyst selected from the group consisting of mixed oxides of Fe, Co, Ni, Bi, P, Mo and K, mixed oxides of Fe, Co, W, Bi, Mo and Mg, mixed oxides of Sb and U, bismuth molybdate, bismuth phosphomolybdate, and mixtures of such catalysts.

2. The process of claim 1 in which the pressure is 1 to 3 atmospheres.

3. The process of claim 1 in which the dehydration catalyst is boron phosphate.

4. The process of claim 1 in which the oxidation catalyst is bismuth phosphomolybdate.

* * * * *